United States Patent [19]

Troeger

[11] Patent Number: 4,901,713
[45] Date of Patent: Feb. 20, 1990

[54] SUPPORTIVE ARM SLING

[76] Inventor: Ursula L. Troeger, 145 Moore Ave., Waterloo, Ontario, Canada, N2J 1X4

[21] Appl. No.: 202,824

[22] Filed: Jun. 6, 1988

[30] Foreign Application Priority Data

Jun. 9, 1987 [CA] Canada ................................. 539165

[51] Int. Cl.$^4$ ............................................. A61F 5/40
[52] U.S. Cl. ..................................................... 128/94
[58] Field of Search ............... 128/94; 2/310, 326–329

[56] References Cited

U.S. PATENT DOCUMENTS

| | | | |
|---|---|---|---|
| 98,564 | 1/1870 | Conklin | 2/327 |
| 211,747 | 1/1879 | Kleinberger | 2/328 |
| 577,757 | 2/1897 | Kern | 2/327 |
| 756,237 | 4/1904 | Hunkins | 2/310 |
| 982,376 | 1/1911 | MacFarlane | 128/94 |
| 1,335,927 | 4/1920 | Ainsworth | 2/310 |
| 1,490,381 | 4/1924 | Gobar | 128/94 |
| 1,842,927 | 1/1932 | Winterbottom | 2/326 |
| 3,108,589 | 10/1963 | Staggs | 128/94 |
| 3,307,538 | 3/1967 | Groll | 128/94 |
| 3,730,164 | 5/1973 | Rash | 128/94 |
| 3,901,579 | 8/1975 | Demerest | 2/326 |

FOREIGN PATENT DOCUMENTS 188606 9/1907 Fed. Rep. of Germany ........ 128/94

Primary Examiner—Robert A. Hafer
Assistant Examiner—Michael Brown
Attorney, Agent, or Firm—R. Craig Armstrong

[57] ABSTRACT

An arm sling is disclosed, having a waistband securable around the waist and a first strap attached to the front and back of the waistband and passable over the shoulder of the slung arm from the unslung side at the back of the waistband to the slung side of the front of the waistband. A second strap is attached to the back of the waistband and is passable over the shoulder of the unslung arm, first crossing the first strap. The first strap bifurcates into two support straps in the area of the slung arm, preferably approximately midway between the shoulder and the waist, to form a substantially triangular shape with the support straps supporting the slung arm at two spaced apart locations, the overall length of the strap and bifurcated support straps being sufficiently long so as to form a loop to cradle the slung arm. The first and second straps preferably are fastened to each other where they cross each other. The sling is preferably sewn and of cotton. The second strap may also have a bifurcated portion, and buckles may be provided at various locations for suitable size adjustments.

12 Claims, 3 Drawing Sheets

SUPPORTIVE ARM SLING

BACKGROUND OF THE INVENTION

1. Field of the Invention

This invention relates to an improved arm sling for supporting an injured or disabled arm horizontally across the body.

Such a sling is useful in cases involving an injury directly to the arm, elbow, wrist, or hand, where it is desireable or essential that the arm be immobilized. The sling is especially useful where the arm or part of it is in a cast, since the sling carries the weight of the arm and case. The sling is also useful in cases where the arm may be disable due to a stroke or any congenital or acquired disability. In short, the sling may be useful in any situation where any conventional arm sling may be used to immobilize and provide support for an arm.

2. Description of the Prior Art

In the prior art, the traditional sling is fashioned from a triangular piece of material, or a piece of material folded into a triangle. The apex of the triangle is positioned near the elbow, and the centre of the base near the hand. The ends at opposite ends of the based are passed on either side of the arm, and then are tied to each other around the person's neck. Most of the weight of the arm is borne by the person's neck and collarbone on the opposite side of the supported arm. This can become very tiring and very uncomfortable, especially if the weight of a cast is involved.

SUMMARY OF THE INVENTION

It is an object of the present invention to provide an improved sling which is simple in construction and which acts to provide better distribution of the weight of the supported arm.

Thus in accordance with the present invention there is provided an arm sling having a waistband securable around the waist and a strap attached to he front and back of the waistband and passable over the shoulder of the slung arm from the unslung side of the back of the waistband to the slung side of the front of the waistband. The strap bifurcates into two support straps in the area of the slung arm to form a substantially triangular shape with the support straps supporting the slung arm at two spaced apart locations, the overall length of the strap and bifurcated support straps being sufficiently long to form a loop to cradle the slung arm. Preferably, a second strap is attached to the back of the waistband and is passable over the shoulder of the unslung arm, first crossing the first strap.

Further features of the invention will be described or will become apparent in the course of the following detailed description.

BRIEF DESCRIPTION OF THE DRAWINGS

In order that the invention may be more clearly understood, the preferred embodiment thereof will now be described in detail by way of example, with reference to the accompanying drawings, in which.

DETAILED DESCRIPTION OF THE PREFERRED EMBODIMENT

Figure 1:
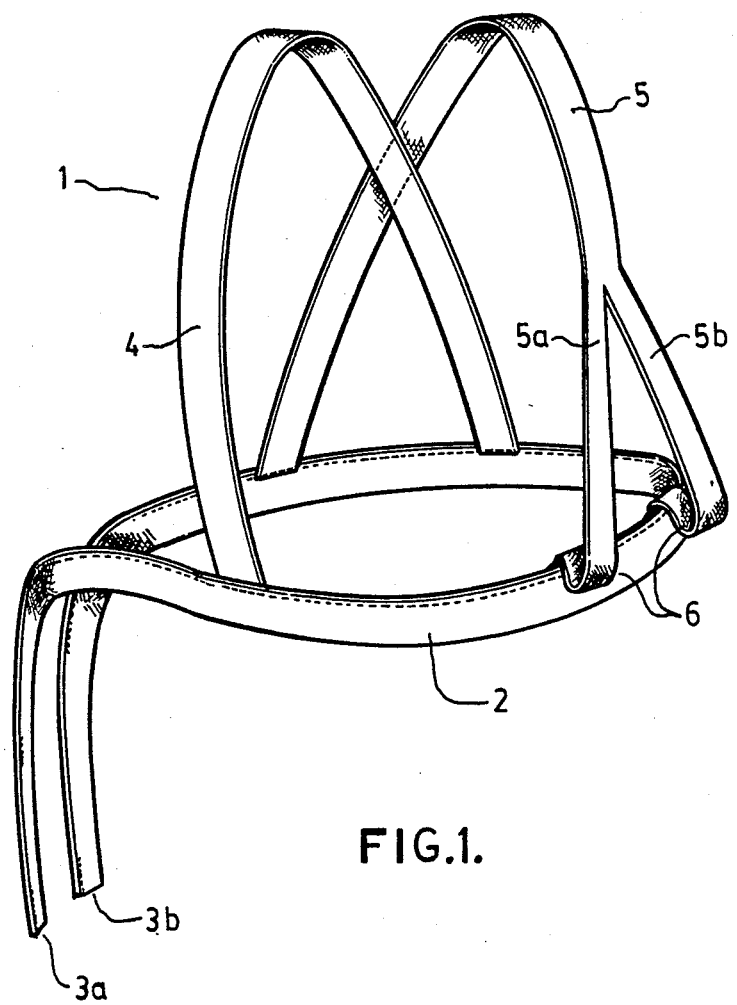
FIG. 1 is a front view of the sling.
Figure 2:
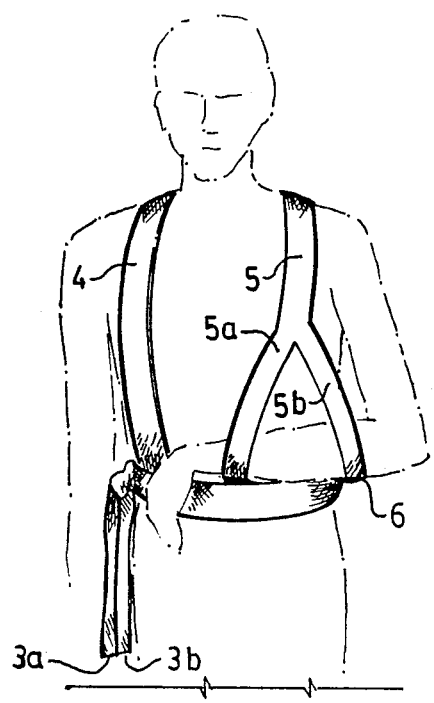
FIG. 2 is a front view of the sling shown supporting a person's arm.

Referring to FIGS. 1 and 2, there is illustrated the sling 1 comprising a waistband 2, having free ends 3a and 3b which are tied or otherwise fastened together to fashion the waistband around a person's waist. From the back of the waistband towards the left side of the person, a strap 4 loops over the right shoulder and down to the front of the waistband towards the right side of the person. From the back of the waistband towards the right side of the person, a strap 5 crosses the strap 4 and loops over the left shoulder down towards the front of the waistband towards the left side of the person. At a point approximately halfway between the shoulder and the waist, the strap 5 becomes bifurcated into two support straps 5a and 5b, which are attached to the waistband 2 at spaced-apart locations on the left front side, defining a roughly triangular shape.

The support straps 5a and 5b are provided with extra length in comparison to the length of the strap 4 in order to form loops 6 which support the arm or cast.

The waistband 2 and straps 4,5 are preferably of cotton, though other materials could of course be used. The waistband and straps are sewn together, preferably including sewing where the first and second straps 4 and 5 respectively cross each other. Naturally, some different connection means could be envisioned, such as hook and pile fastening, or snaps or buttons or the like, but sewing is preferred for its simplicity.

The advantages of this arrangement are several. Firstly, by virtue of the two straps and waistband, the weight of the cast or arm is more evenly distributed, for greater comfort and improved posture. Secondly, the two support straps 5a and 5b being spaced apart ensures that the arm or cast is supported at spaced-apart locations, ensuring greater stability than with conventional slings, where in practice one portion of the sling tends to carry most of the weight.

Typical dimensions which have been found suitable are as follows:

TABLE 1

| TYPICAL DIMENSIONS | |
|---|---|
| Strap and waistband width: | 6.5 cm. |
| Waistband length: | 177 cm. |
| Length of strap 4 (to top of waistband): | 84 cm. |
| Length of strap 5 (incl. bifurcated portions): | 88 cm. |
| Bifurcated portion length: | 26 cm. |
| Centre to centre spacing between: | |
| Straps 4 and 5 at rear of waistband | 12 cm. |
| Strap 4 at rear and nearest support strap 5b: | 20 cm. |
| Support straps 5a and 5b: | 14 cm. |
| Support strap 5a and first strap 4 at front: | 17 cm. |

Obviously, these dimensions can be varied to provide various desired sizes.

The sling can be used for either arm, simply by turning it inside out. This is slightly difficult to visualize, but turning the sling inside out produces exactly the same structure, just oriented for the other arm.

Figure 3:
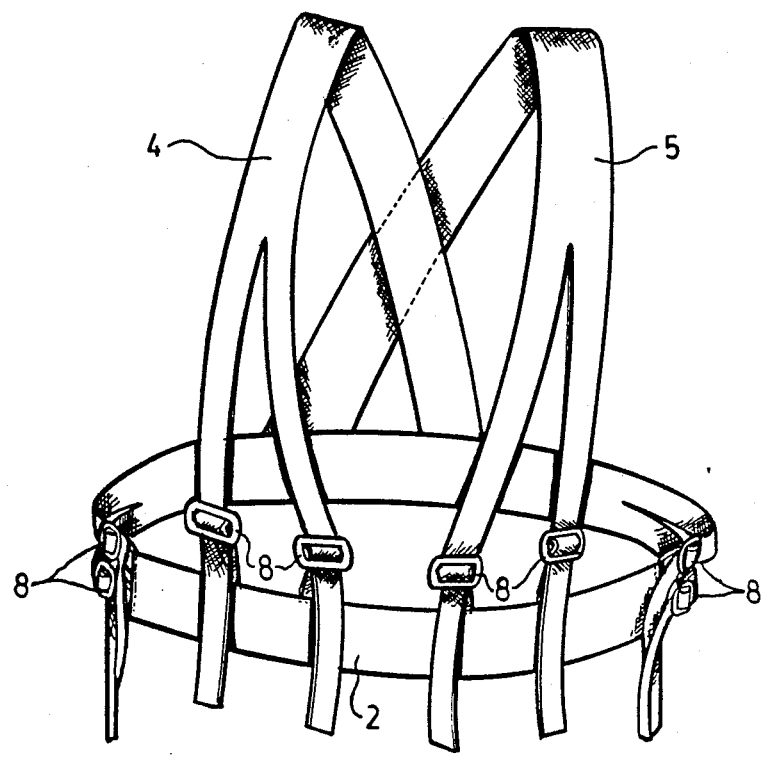
FIG. 3 is a front view of an alternative embodiment of the sling.

Alternatively, a double-sided sling can be used, as illustrated in FIG. 3, in which each side is provided with bifurcated portions. Various buckles 8 can be used to permit adjustment of each of the bifurcated portions, as well as the waistband. The waistband may itself be bifurcated leading up to the location of the buckles, to provide greater flexibility and comfort.

The above description relates to the preferred embodiment by way of example only. Many variations on the invention will be obvious to those knowledgeable in the field, and such obvious variations are within the scope of the invention, whether or not expressly described.

What is claimed as the invention is:

1. An arm sling comprising:
   a waistband securable around a user's waist;
   a strap attached to the front and back of the waistband and passable over a user's shoulder of the slung arm from the unslung side back of the waistband to the slung side of the front of the waistband, said strap being a single strip of maerial that is bifurcated into two support straps in the area of the slung arm at a point a distance above the waistband, said distance at least one-eighth the length between the shoulder and the waistband, to form a substantially triangular shape with the support straps supporting the slung arm at two spaced apart locations, the overall length of the strap and bifurcated support straps being sufficient to form a loop to cradle the slung arm.

2. An arm sling as recited in claim 1, further comprising a second strap attached to the back of the waistband on the side of the slung arm, crossing said first strap, passable over the shoulder of the unslung arm, and attached to the front of the waistband on the unslung side.

3. An arm sling as recited in claim 2, in which said first and second straps are fastened to each other where they cross each other.

4. An arm sling as recited in claim 3, in which said waistband and said first and second straps, including said support straps, are of cotton and are attached or fastened by sewing.

5. An arm sling as recited in claim 2, in which said waistband and said first and second straps, including said support straps, are of cotton and are attached or fastened by sewing.

6. An arm sling as recited in claim 2, in which said second strap is bifurcated in a manner similar to the bifurcation of said first strap.

7. An arm sling recited in claim 6, in which said waistband and said first and second straps, including support straps, are of cotton and are attached or fastened by sewing.

8. An arm sling as recited in claim 1, in which the first strap bifurcates approximately midway between the shoulder and the waist.

9. An arm sling as recited in claim 8, in which said first and second strap are fastened to each other where they cross each other.

10. An arm sling as recited in claim 9, in which said waistband and said first and second straps, including said support straps, are of cotton and are attached or fastened by sewing.

11. An arm sling as recited in claim 8, in which said waistband and said first and second straps, including said support straps, are of cotton and are attached or fastened by sewing.

12. An arm sling as recited in claim 1, in which said waistband and said first and second straps, including said support straps, are of cotton and are attached or fastened by sewing.

* * * * *